(12) United States Patent
Pouteau et al.

(10) Patent No.: US 11,027,277 B2
(45) Date of Patent: Jun. 8, 2021

(54) DEVICE FOR COLLECTING A LIQUID SAMPLE BY CAPILLARITY

(71) Applicant: AVALUN, Grenoble (FR)

(72) Inventors: Patrick Pouteau, Meylan (FR); Vincent Poher, Guines (FR)

(73) Assignee: AVALUN, Grenoble (FR)

( * ) Notice: Subject to any disclaimer, the term of this patent is extended or adjusted under 35 U.S.C. 154(b) by 947 days.

(21) Appl. No.: 15/554,783

(22) PCT Filed: Feb. 26, 2016

(86) PCT No.: PCT/FR2016/050446
§ 371 (c)(1),
(2) Date: Aug. 31, 2017

(87) PCT Pub. No.: WO2016/139409
PCT Pub. Date: Sep. 9, 2016

(65) Prior Publication Data
US 2018/0050339 A1  Feb. 22, 2018

(30) Foreign Application Priority Data

Mar. 2, 2015 (FR) ...................................... 1551725

(51) Int. Cl.
*B01L 3/00* (2006.01)
*A61B 5/15* (2006.01)
(Continued)

(52) U.S. Cl.
CPC ........ *B01L 3/50273* (2013.01); *A61B 5/1405* (2013.01); *A61B 5/157* (2013.01); *A61B 5/150022* (2013.01); *A61B 5/150061* (2013.01); *A61B 5/150343* (2013.01); *A61B 5/150755* (2013.01); *A61B 10/007* (2013.01); *A61B 10/0045* (2013.01); *B01L 2200/141* (2013.01); *B01L 2300/042* (2013.01); *B01L 2300/069* (2013.01); *B01L 2300/0627* (2013.01);
(Continued)

(58) Field of Classification Search
None
See application file for complete search history.

(56) References Cited

U.S. PATENT DOCUMENTS

2016/0022189 A1* 1/2016 Pouteau ........... A61B 5/150022
600/583

FOREIGN PATENT DOCUMENTS

DE  43 07 735  9/1993
FR  3003033 A1 * 9/2014 ....... A61B 5/150358
(Continued)

OTHER PUBLICATIONS

Giléré, Alain and Cyril Delattre, "Modeling and Fabrication of Capillary Stop Valves for Planar Microfluidic Systems," Sensors and Actuators, A 130-131, pp. 601-608 (2006).

*Primary Examiner* — Lyle Alexander
*Assistant Examiner* — Bryan Kilpatrick
(74) *Attorney, Agent, or Firm* — Occhiuti & Rohlicek LLP

(57) ABSTRACT

A device for collecting a liquid sample by capillarity includes distinct first and second elements having respective male and female parts. The male part comprises a channel having a transverse section. The female part comprises a peripheral wall that transversely delimits a cavity to house the male part. A part of the peripheral wall forms a cap to close the transverse section when the female part houses the male part.

20 Claims, 9 Drawing Sheets

(51) Int. Cl.
*A61B 5/157* (2006.01)
*A61B 10/00* (2006.01)
(52) U.S. Cl.
CPC .................. *B01L 2300/0645* (2013.01); *B01L 2400/0406* (2013.01)

(56) References Cited

FOREIGN PATENT DOCUMENTS

| WO | WO 96/33399    | 10/1996 |
| WO | WO 01/05505    | 1/2001  |
| WO | WO 2005/020817 | 3/2005  |
| WO | WO 2014/135652 | 9/2014  |

* cited by examiner

DEVICE FOR COLLECTING A LIQUID SAMPLE BY CAPILLARITY

RELATED APPLICATIONS

This is the national stage of PCT/FR2016/050446, filed on Feb. 26, 2016, which claims the Mar. 2, 2015 priority date of French application 1551725, the contents of which are herein incorporated by reference.

FIELD OF INVENTION

The field of the invention is that of collecting liquid samples for analysis, for example chemical and/or biological samples. The invention relates to a device for collecting a liquid sample, comprising a channel in which the sample is intended to flow by capillarity, and to a method for analyzing the liquid sample collected by means of such a device.

BACKGROUND

In many cases, it is desirable to collect liquid samples for analysis. One way to do so is to reply on capillary action, or "capillarity."

Exploiting capillarity often includes providing an opening that leads into a channel through which liquid moves by capillarity. This channel is sometimes difficult to access. This makes functionalization of the channel difficult.

In addition, the channel is sometimes exposed to the environment. This can lead to contamination.

SUMMARY OF THE INVENTION

Among the objectives of the invention is an apparatus for collecting a liquid sample by capillarity in such a way that there is simplified access to the internal surfaces of the channel and an effective containment of the channel.

In one aspect, an apparatus for collecting a liquid sample by capillarity includes a first element comprising a male part and a second element that is distinct from the first element and that comprises a female part. The male part has a channel with an open transverse section. The channel extends longitudinally between a first input end and a second end. The channel is formed by a channel-bottom longitudinal wall bordered by two lateral walls that form its sides. The female part has a peripheral wall that transversely delimits a cavity intended to house the male part. Part of the peripheral wall forms a cap when the female part houses the male part. This cap closes the transverse section of the channel.

Preferably, at least one of the sides of the channel is arranged such that, when the female part houses the male part, the distance, between two walls of the channel, in a plane transverse to the longitudinal axis of the channel, decreases towards a transverse edge of the channel.

The male part can be formed by a plate of substantially rectangular transverse section, the channel being disposed at the level of a top longitudinal face of the plate forming the male part.

The channel can comprise an analysis chamber disposed at the level of the top face of the male part or at the level of a bottom face opposite the top face of the male part.

According to one embodiment, the channel comprises at least one analysis chamber, with open transverse section, disposed at the level of the bottom face of the male part, communicating with the portion of the channel situated at the level of the top face, and in which a part of the peripheral wall of the female part is inserted, when the female part houses the male part, to form a second cap closing the transverse section of the analysis chamber.

The analysis chamber can communicate with the portion of the channel situated at the level of the top face by a duct emerging at the level of a central zone of the analysis chamber.

In some embodiments, the dimensions of the male part and those of the female part defining the cavity are chosen such that, when the female part houses the male part, the cap bears on the top face of the plate of the male part or vice versa, and possibly on the bottom face opposite the top face, to ensure the hermetic sealing of the transverse section of the channel.

In some embodiments, at least a portion of the surface of the bottom longitudinal wall, at least a portion of the sides of the channel, and/or at least a portion of the surface of the cap has or have a wettability that differs from that of the other surfaces of the channel.

In some embodiments, the second element comprises a contact surface to receive the liquid sample, assembled with the female part, such that a collection opening of the cavity emerges at the level of the contact surface, and in which, when the female part houses the male part, an end transverse wall of the male part at the level of which is located the first input end of the channel, is flush with the contact surface.

In some embodiments, the second end of the channel communicates with a vent emerging into the environment of the device.

In some embodiments, the first element comprises a gripping heel on which the male part is assembled. The heel can be formed by a plate that extends in the plane of the male part and that comprises at least one protruding portion facing the plate of the heel. The heel can comprise a surface intended to form an abutment with respect to the peripheral wall of the female part when the female part houses the male part.

In some embodiments, the channel comprises at least one portion forming an analysis chamber comprising dried or freeze-dried reagents, at least one electrode, or one absorbent membrane.

The channel can be delimited transversely by delimiting lateral-walls configured to be in contact with the cap, the latter segregating the channel from a peripheral zone that at least partly surrounds the channel, the channel comprising a bottom surface facing the cap and the peripheral zone comprising a peripheral surface facing the peripheral wall, a distance between the peripheral surface and the facing peripheral wall, along an axis orthogonal to the bottom surface, being greater than a distance between the bottom surface and the facing cap.

The invention relates also to a method for producing a liquid sample using a sample-collecting device according to any one of the preceding features. Such a method includes producing a first element comprising a male part, the latter comprising at least one channel with open transverse section, extending longitudinally between a first input end and a second end, the channel being formed by a channel-bottom longitudinal wall bordered by two lateral walls forming the sides of the channel; producing a second element, distinct from the first element and comprising a female part, the latter comprising a peripheral wall that transversely delimits a cavity intended to house the male part, a part of the peripheral wall being intended, when the female part houses the male part, to form a cap closing the transverse section of the channel; functionalizing a zone of the channel forming an analysis chamber; and introducing the male part into the female part.

BRIEF DESCRIPTION OF THE DRAWINGS

These and other features and advantages will be apparent from the following detailed description and the accompanying figures, in which.

DETAILED DESCRIPTION

Figure 1:
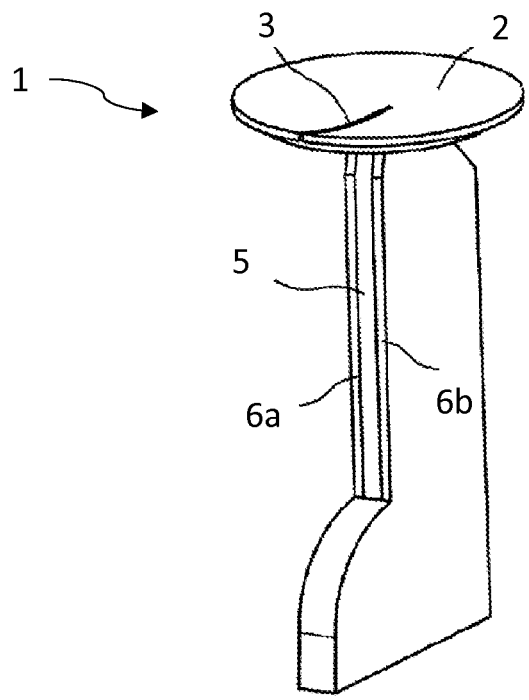
FIGS. 1 and 2 show a device that uses capillarity to collect a liquid sample.
Figure 2:
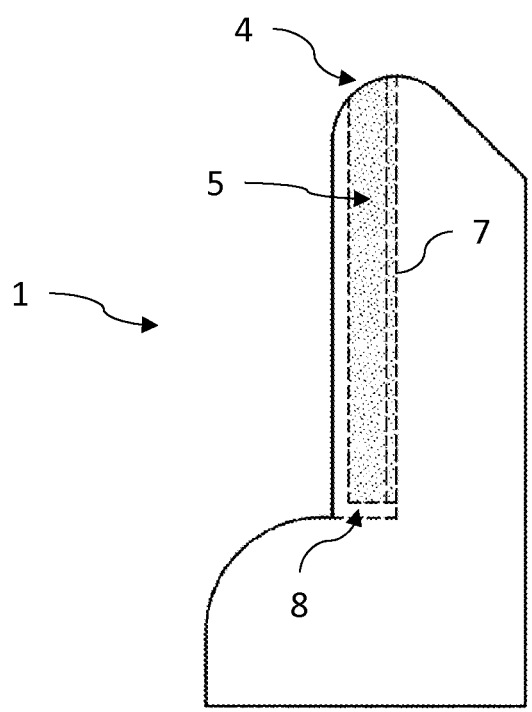

FIGS. 1 and 2 illustrate an example of a sample-collection device 1 for collecting a liquid sample by capillary action, also referred to herein as "capillarity." The sample-collection device 1 comprises a contact surface 2 having a through opening 3 that emerges at an input end 4 of a channel 5 that extends longitudinally between the input end 4 and a second end 8. First and second lateral walls 6a, 6b that are parallel to one another and that are linked to one another by a bottom wall 7 form the channel 5.

The bottom wall 7 is arranged such that the distance between the two lateral walls 6a, 6b decreases towards the bottom of the channel 5. Thus, when a liquid sample is deposited on the contact surface 2, it enters the channel 5 at the input end 4 and flows by capillary action along the channel 5 to the second end 8. The motive force is a capillary force whose intensity is augmented by the converging of the lateral walls 6a, 6b at the level of the bottom. A flow-stopper stops the flow of the liquid at the second end 8 of the channel 5. A suitable flow-stopper is a hydrophobic zone or a sudden widening of the dimensions of the channel 5.

The channel 5 usually comprises a measurement or analysis chamber in which dried or freeze-dried reagents or electrodes are provided. Since the lateral walls 6a, 6b of the channel 5 are generally transparent to visible or infrared radiation, an optical measurement can be performed for the chemical or biological analysis of the liquid sample or of the chemical reaction initiated when the dried or freeze-dried reagent is taken up by the sample.

The channel 5 has an open transverse section. As a result, the channel 5 is open to the environment over all of its longitudinal part opposite the bottom wall 7.

One drawback of the sample-collection device 1 is that the internal surfaces of the channel 5 are difficult to access, particularly when there is a desire to functionalize them by the deposition of dried or freeze-dried reagents or by the placement of electrodes or by a localized chemical or biological treatment on the surface. As an example, in the case of the functionalization of the analysis chamber by dried or freeze-dried reagents, the difficulty of accessing the analysis chamber makes the deposition and drying of the reagents difficult to carry out and also difficult to reproduce.

One way to circumvent this difficulty is to introduce a solvent containing the reagents at the input end 4 of the channel 5 and to have it to flow to the analysis chamber before proceeding with the evaporation or the sublimation of the solvent.

The interior of the channel 5 is accessible from the outside over all of its open longitudinal part. This increases the risk of pollution of the channel 5 by an outside element, and may require the interior of the channel 5 to be structured so as to form means for anchoring the liquid intended to contain the liquid sample inside the channel 5 and thus avoid a contamination of the external medium by the liquid.

Figure 3:
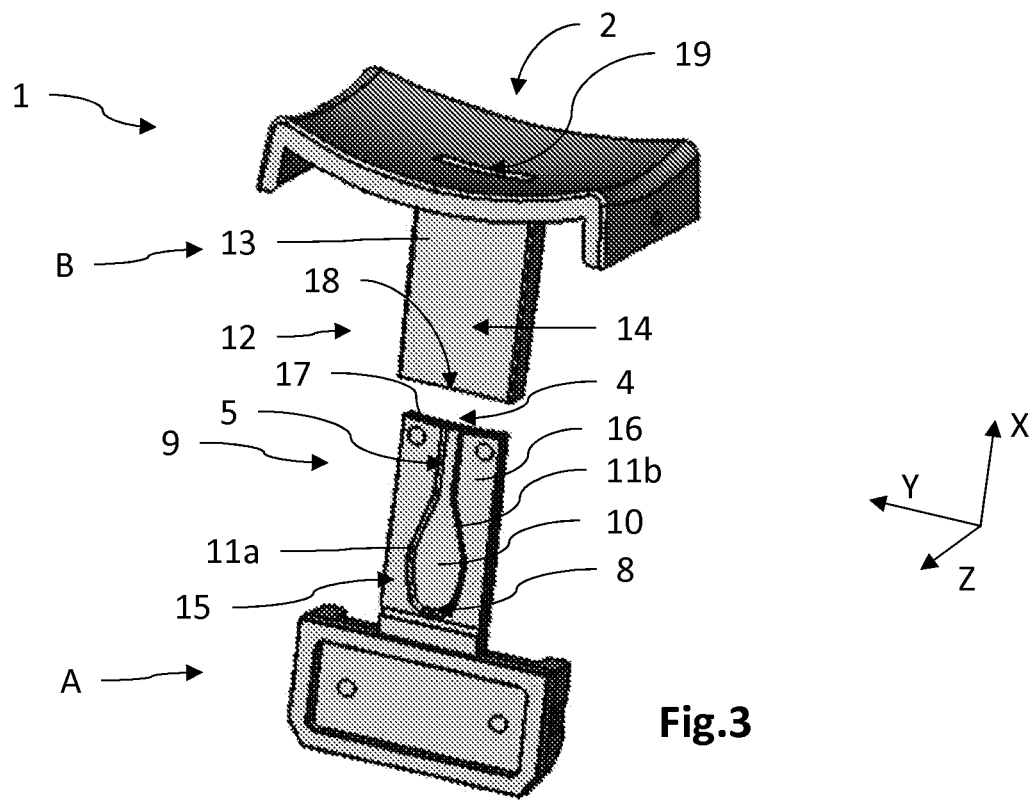
FIG. 3 is a perspective view of a device for collecting a liquid sample according to one embodiment, in which the male part is disengaged from the female part.

FIG. 3 illustrates a sample-collection device 1 for collecting a liquid sample by capillarity, according to an embodiment.

The sample-collecting device 1 comprises first and second elements A, B that are distinct from one another and that cooperate with one another to make the sample-collection device 1 operational.

The first element A comprises a male part 9 at the level of which there is a channel 5 with open transverse section. The channel 5 extends longitudinally between a first end 4 and a second end 8. The first end 4 is an input end that receives a liquid sample. The channel 5 is formed by a longitudinal wall 10, hereinafter in the description called bottom wall, bordered by two lateral walls 11a, 11b that form the sides of the channel 5.

The second element B comprises a female part 12 formed by a peripheral wall 13 that transversely delimits a cavity intended to house or receive the male part 9. Furthermore, when the female part 12 houses the male part, a part of the longitudinal wall 13 forms a cap 14 that closes the transverse section of the channel 5.

Operating the sample-collection device 1 includes introducing the male part 9 of the first element A into the female part 12 of the second element B such that the peripheral wall 13 closes the transverse section of the channel 5, preferably over all the length of the channel 5. A liquid sample can then be brought into contact with the input end 4 of the channel 5, thereby inducing it to engage in capillary flow along the channel 5 towards the second end 8.

Having two distinct elements A and B of the sample-collecting device 1 in which the channel 5 has a longitudinally open transverse section results in direct access to the channel's interior before insertion of the male part 9 into the female part 12 as well as better containment of the channel 5 following insertion of the male part 9 into the female part 12, in a better containment of the channel 5.

The direct access to the interior of the channel 5 makes it possible to functionalize and/or treat the interior of the channel 5, partly or totally, with a simplicity and effectiveness that the prior art does not achieve.

Thus, in the case where there is desire to deposit into the channel 5 a dried or freeze-dried reagent intended to interact with the liquid sample, the direct access to the interior of the channel 5 makes it possible to proceed simply and rapidly with a particularly uniform deposition of the reagent. In effect, the interior of the channel 5 is directly accessible over all of its length, whereas, in the prior art, the channel 5 is accessible only from its input end 4. The accuracy of positioning of the tools for depositing the reagent or reagents to be dried or freeze-dried can then be simplified. It is also possible to perform a localized deposition of the reagent or reagents to be dried or freeze-dried, directly in a desired zone of the channel 5 (whether at the input, in the middle or at the output of the channel 5) simply. The example from the prior art does not offer such simplicity in the localized positioning of the reagent or reagents.

It is also possible to deposit, within the channel 5, one or more electrodes or an absorbent membrane. In addition, it is possible to chemically functionalize the interior of the channel 5, for example by locally immobilizing one or more molecules or biological entities directly on a wall of the channel 5, for example by covalent chemical bond. Such molecules or entities include, without limitation, proteins, DNA sequences, antibodies, etc.

The sample-collecting device 1 also offers, when the female part 12 houses the male part 9, a particularly effective containment of the channel 5. This makes it possible to limit, and even avoid, the contamination of the outside environment by the liquid present in the channel 5 as well as the pollution of the channel 5 from the outside.

In the example of FIG. 3, the male part 9 is formed by a plate 15 having a substantially rectangular transverse section. The channel 5 is arranged at the level of a longitudinal top face 16 of the plate such that the input end 4 of the channel 5 emerges on an end transverse wall 17 of the plate 15. In the illustrated embodiment, the plate 15 has a rectangular transverse section. But any section can be used, including but not limited to square and circular sections.

A three-dimensional orthonormal reference frame is defined as illustrated in FIG. 3, in which the X axis is oriented along the longitudinal axis of the male part 9, the Y axis along its width and the Z axis along its thickness. The width of the channel 5 is defined as the distance, along the Y axis, between two walls of the channel 5, and the depth of the channel 5 is defined as the distance, along the Z axis, between two walls of the channel 5.

The bottom longitudinal wall 10 of the channel 5 advantageously has a dimension, in transverse cross section, greater than that of each of the sides 11a, 11b. In other words, the transverse form factor of the channel 5, namely the ratio of the width of the channel 5 to its depth, is, in this example, strictly greater than 1, preferably greater than 5, and even greater than 10.

In the example of FIG. 3, the peripheral wall 13 of the female part 12 extends longitudinally, along the X axis, so as to form a cavity capable of receiving and housing, preferably entirely, the male part 9. Furthermore, the internal dimensions of the peripheral wall 13 are adjusted such that the surface of the outline of the male part 9 comes into contact with the internal surface of the peripheral wall 13, when the female part 12 houses the male part 9.

In this example, the peripheral wall 13 forms a cavity of substantially rectangular transverse section in the Y-Z plane corresponding to the rectangular transverse section of the male part 9. However, any other form complementing that of the male part 9 is suitable.

In a particular embodiment, the transverse section of the peripheral wall 13 exhibits, along the X-axis, a homothetic reduction of these dimensions and of the transverse section of the male part 9. This allows for a cone-cone type fitting that simplifies the assembly of the two elements of the sample-collection device 1.

The cavity extends between an insertion opening 18, through which the male part 9 is intended to be introduced, and an opposite collection opening 19 capable of receiving the liquid sample for the insertion thereof into the channel 5.

The second element B further comprises a contact surface 2, here in the form of a cup, intended to receive the liquid sample. The female part 12 is assembled with the contact surface 2 such that the collection opening 19 of the cavity emerges at the level of the contact surface 2. The contact surface 2 extends substantially orthogonally to the female part 12 and can have a curved, flared, more specifically convex form, to make it possible to facilitate the contacting of the liquid sample with the collection opening 19. This curve is also particularly suited to the deposition of a drop hanging at the end of a human finger such that it can be presented when collecting a capillary sample of blood at the end of a finger.

When a liquid sample is deposited on the contact surface 2 and comes into contact with the collection opening 19, it is introduced by capillarity into the channel 5 through its input end 4. When the contact surface 2 has a flared form, as represented in FIG. 3, it is advantageous for the end transverse wall 17 of the male part 9 to also have a curved form of the same radius of curvature. Thus, the contact surface 2 and the surface of the end transverse wall 17 of the male part 9 together present a substantially continuous surface with no unevenness protruding or set back other than the opening of the input end 4 of the channel 5.

To promote the introduction of the liquid sample by capillarity into the channel 5, the walls of the sample-collecting device 1 ideally exhibit a wetting angle less than 90° and ideally less than 50°. This can be obtained by choosing materials that naturally exhibit this wetting angle or else by chemical treatment after the elements A and B of the sample-collection device 1 have been manufactured. An oxygen plasma treatment or even an insolation treatment with an intense UV lamp in the presence of oxygen can also be used.

Figure 4:
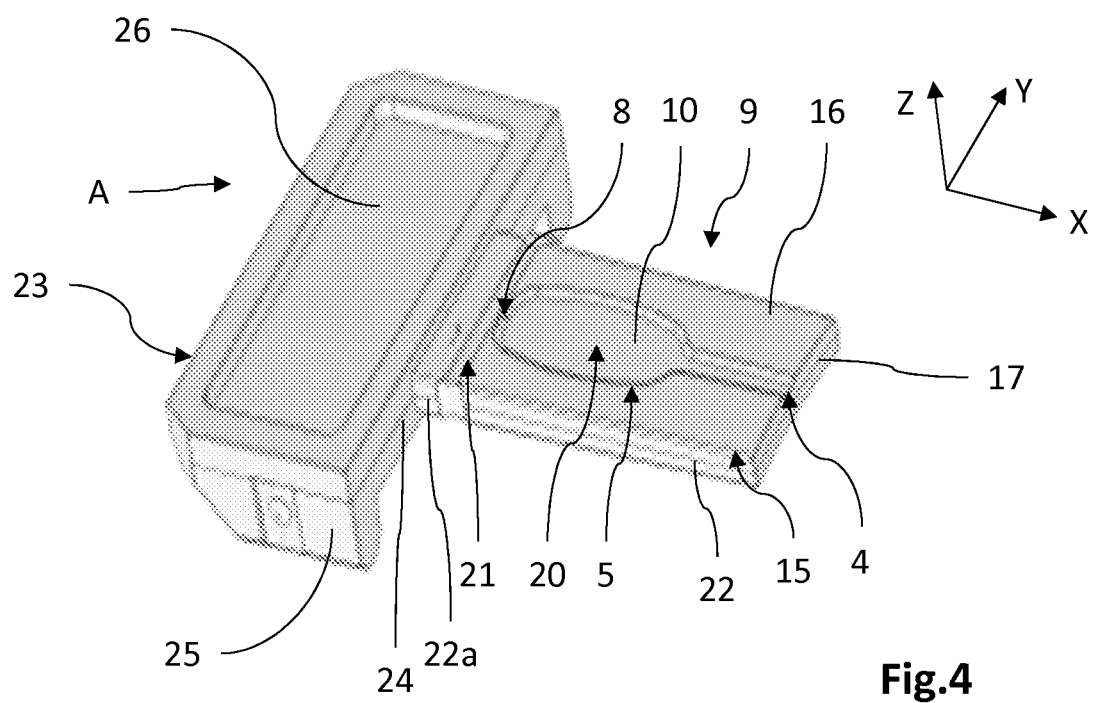
FIG. 4 is a perspective view of the first element of the sample-collecting device represented in FIG. 3.

FIG. 4 is a detailed and perspective view of the first element according to the embodiment represented in FIG. 3.

The channel 5, which is arranged at the level of the top face 16 of the male part 9, extends between the input end 4 and the second end 8. The channel 5 comprises a first portion that extends from the input end 4 and a second portion 20 that extends to the second end 8 of the channel 5. The second portion 20 has a width that increases along the Y-axis. This second portion 20 forms an analysis chamber or a measurement chamber. Such a chamber permits analysis of or measurement of parameters associated with a liquid in the analysis chamber.

At the level of the second end 8, the channel 5 communicates with a vent 21 that allows the channel 5 to be connected to the open air. The vent 21 extends to an edge of the plate forming the male part 9. In this example, the vent 21 is a groove formed in the top face 16 of the male part 9 and extends along the Y-axis so as to join the two longitudinal edges 22 of the male part 9. When the female part 12 houses the male part 9, the peripheral wall 13 of the female part 12 comprises at least one emergent opening that communicates with the vent so as to allow the channel 5 to be connected to the open air.

The channel 5 comprises, at the level of its second end 8, a flow-stopping mechanism that stops liquid flow. Examples of a stopping mechanism take the form of a zone in which at least a part of the internal surfaces of the channel 5 are hydrophobic with respect to the liquid sample. This hydrophobic property can be obtained by a localized surface treatment or by the deposition of a hydrophobic coating. It can affect all or part of the sides, cap and bottom of the channel 5. It can also, as in the case of FIG. 4, take the form of a widening of the transverse dimensions of the channel 5, for example its width along the Y-axis. This widening makes it possible to reduce the capillary force of wettability responsible for the flow of the liquid. The flow-stopping mechanism can also be a closing wall of the channel 5 that extends in a transverse section of the channel 5 and blocks the flow in the longitudinal direction of the channel 5.

The dimensions of the male part 9 and those of the cavity of the female part 12 are such that, when the female part 12 houses the male part 9, the male part 9 and the female part 12 engage each other by surface friction. In the example of FIG. 4, the male part 9 comprises a part of its longitudinal edges 22 whose width along the Z-axis, and possibly along the Y-axis, increases with distance away from the input end 4 of the channel 5. Thus, when the female part 12 houses the male part 9, the peripheral wall 13 of the female part 12 exerts a pressing force on these widened lateral parts 22a of the male part 9 and will thus be held by friction at the level thereof.

Moreover, the dimensions of the male part 9 and those of the cavity of the female part 12 are such that, when the female part 12 houses the male part 9, the cap 14 bears on the top face 16 of the male part 9 or vice versa so as to ensure the hermetic sealing of the transverse section of the channel 5.

The first element A further comprises a gripping heel 23 on which the male part 9 is fixed. The heel 23 takes the form of a plate that extends primarily in the X-Y plane of the male part 9 along a longitudinal axis, i.e., the Y-axis, substantially orthogonal to the longitudinal axis, i.e., the X-axis, of the male part 9. It allows a user to easily handle the sample-collection device 1.

The heel 23 comprises, on either side of the male part 9, a surface intended to form an abutment 24 with respect to the peripheral wall 13 of the female part 12, when the male part 9 is introduced into the female part 12. The longitudinal dimensions of the male part 9 and of the female part 12 are substantially equal, such that, when the female part 12 houses all of the male part 9, the end of the peripheral wall 13 delimiting the insertion opening 18 is in contact with the abutment 24 of the heel 23 and the end transverse wall 17 of the male part 9 is located at the level of the collection opening 19 of the cavity, the input end 4 of the channel 5 being flush with the contact surface 2.

The heel 23 also comprises at least one protruding portion 25, and in the illustrated embodiment two portions, that extend transversely to the Y-Z plane of the heel 23. These portions 25 ensure a polarizer function making it possible to avoid any error in the use or the handling of the sample-collecting device 1, particularly with respect to correctly placing the sample-collection device 1 in a support of an analysis system.

Figure 7:
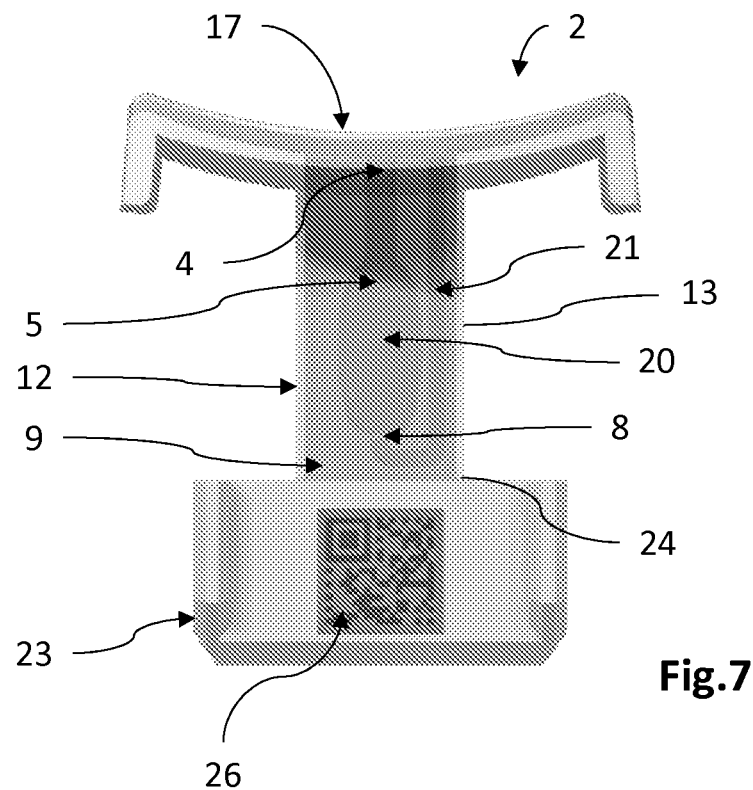
FIG. 7 is a front view of a sample-collecting device whose male part is introduced into the female part, according to an embodiment in which the vent emerges at the level of the contact surface.
Figure 8:
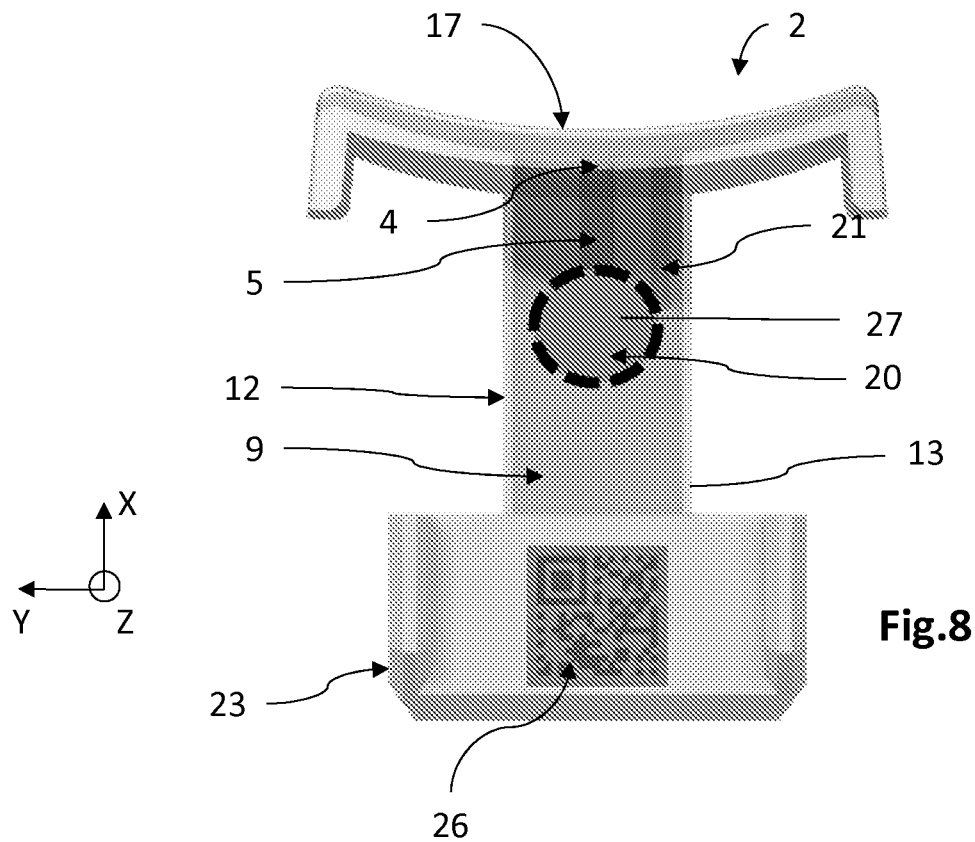
FIG. 8 is a front view of a sample-collecting device whose male part is introduced into the female part, according to an embodiment in which an analysis chamber of the channel comprises an absorbent membrane.

Moreover, as FIGS. 7 and 8 illustrate, the heel 23 comprises an information inscription zone 26 where information can be inscribed in the form, for example, of a QR code (or data matrix code), for example making it possible to identify the type of reagent deposited in the analysis chamber 20 of channel 5 and/or a date of expiry or of production.

Figure 5:
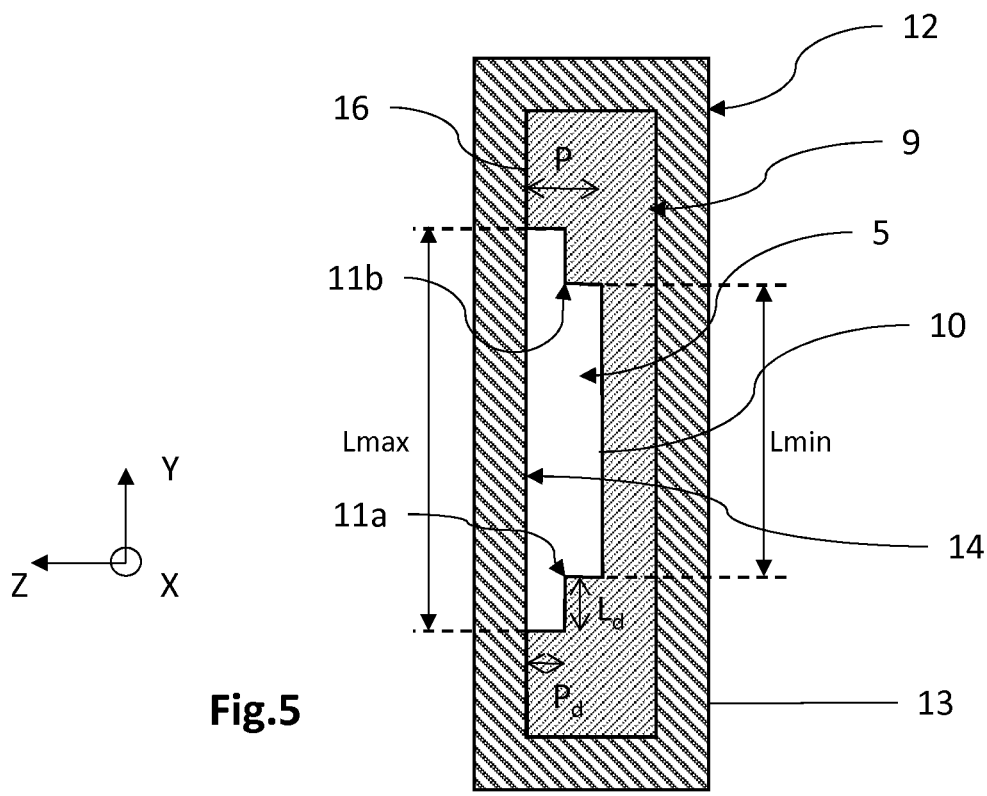
FIGS. 5 and 6 are schematic views in transverse cross section of the channel of the sample-collecting device according to two embodiments.
Figure 6:
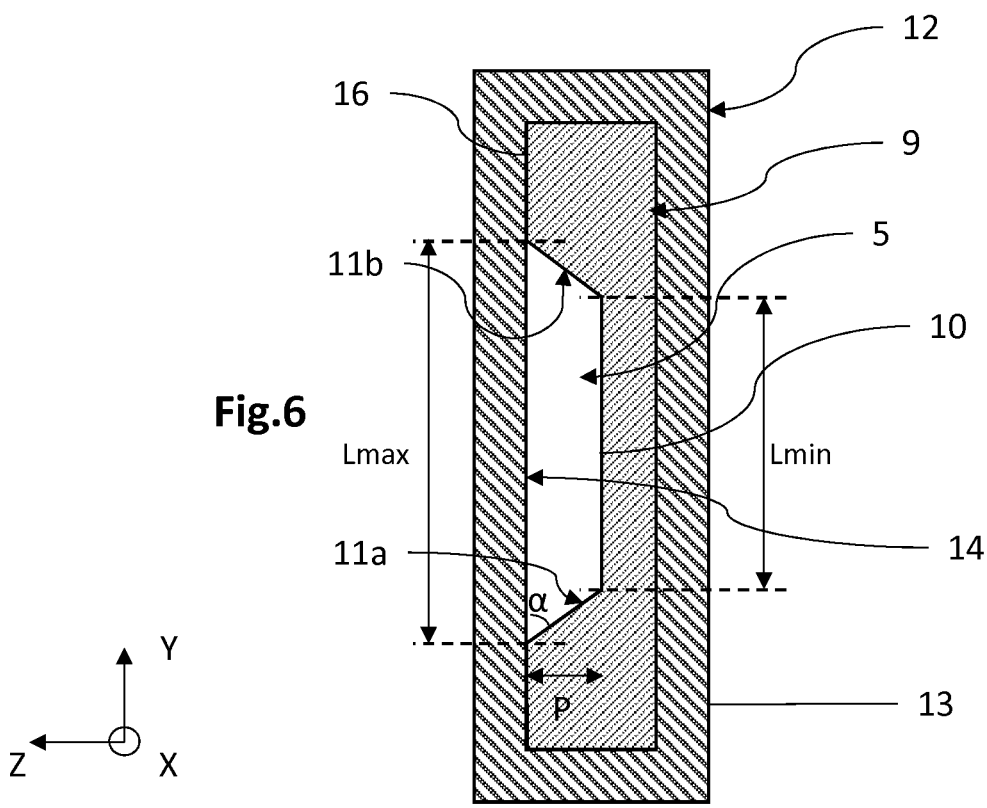

FIGS. 5 and 6 are schematic views of the channel 5, in transverse cross section, when the female part 12 houses the male part 9, according to two variant embodiments.

The three-dimensional orthonormal reference frame defined in FIG. 3 is reproduced here. The X-axis is oriented along the length of the male part 9, the Y-axis along its width, and the Z-axis along its thickness. It will be recalled that the width of the channel 5 is defined as the distance, along the Y-axis, between two walls of the channel 5, and the depth of the channel 5 as the distance, along the Z-axis, between two walls of the channel 5. The transverse edges of the channel 5 are the ends of the latter in the Y-Z plane along the Y-axis.

The male part 9 has a transverse section open in the Y-Z plane formed by a bottom wall 10 bordered at its two longitudinal ends by lateral walls 11a, 11b forming sides of the channel 5. The female part 12 comprises a part of its peripheral wall 13 that forms a cap 14, the internal face of the latter coming into contact with the top face 16 of the male part 9 so as to close the transverse section of the channel 5.

So as to increase the intensity of the capillary force that ensures the flow of the liquid sample in the channel 5, it is advantageous to arrange, that is to say incline or structure, at least one of the sides 11a, 11b of the channel 5 so that, when the female part 12 houses the male part 9, the distance, in a transverse plane, or Y-Z plane of the channel 5, between two walls of the channel 5, decreases towards a transverse edge, along the Y-axis, of the channel 5. In other words, the depth of the channel 5 decreases at the level of one of the edges of the channel 5, preferably over all the length of the channel 5 to the second end 8. Thus, a local narrowing of the channel 5 is formed at the level of at least one edge of the channel 5 capable of generating a capillary force of stronger intensity, which results in a greater liquid flow velocity.

FIG. 5 illustrates an embodiment in which the cap 14 and the bottom wall 10 are planar and parallel to one another. The sides 11a, 11b are structured so as to form a recess coming into contact with the cap 14. Thus, at the level of the recess, the depth $P_d$ of the channel 5, therefore, here, the distance along the Z-axis between the cap 14 and the part of the side parallel to the cap 14, is less than the central depth P measured between the cap 14 and the bottom wall 10. A local narrowing is therefore produced at the level of the edges of the channel 5, conducive to allowing a faster flow of the liquid sample in the channel 5.

Preferably, to generate a spontaneous capillary flow, the dimensions of the recess satisfy the following condition:

$$L_d > P_d/2(1/\cos(\theta)-1)$$

in which $L_d$ is the width of the recess along the Y-axis, that is to say the distance between the elbow of the recess and the bottom thereof, $P_d$ the depth of the channel 5 at the level of the recess, and $\theta$ the wetting angle that the liquid forms on the internal surface of the channel 5, at the level of the triple point. It is assumed here that the wetting angle is the same for all the walls of the channel 5. As an example, the depth $P_d$ of the recess is less than or equal to 1 mm, even than 500

µm, and preferably lies between 30 µm and 500 µm, even between 100 µm and 200 µm. The width $L_d$ is preferably less than a few millimeters, for example less than 1 mm, even less than 0.7 mm, and in particular between 200 µm and 500 µm.

FIG. 6 illustrates another embodiment of the transverse form of the channel 5, in a variant to the embodiment of FIG. 5, that differs from the latter only by the arrangement of the sides 11a, 11b of the channel 5. In this example, the sides 11a, 11b are substantially planar and inclined so as to form an acute angle, less than 90°, with the cap 14. The localized narrowing of the channel 5 here takes the form of a V at the level of the edges. The depth at the edge of the channel 5 is then defined by the distance along the Z-axis between the cap 14 and the side 11a, 11b concerned.

Preferably, to obtain a capillary flow deriving from a Concus-Finn effect, the inclination of the sides 11a, 11b satisfies the following condition:

$$\theta < \pi/2 - \alpha$$

in which θ is the wetting angle defined previously and a the angle of inclination of the side concerned 11a, 11b in relation to the cap 14. Thus, this arrangement of the sides of the channel 5 in the form of a V makes it possible to generate a "point effect" at the level of the interface of the liquid sample, which makes it possible to increase the liquid flow velocity in the channel 5.

In this example, by way of illustration, the depth of the channel 5 is 150 µm, the width $L_{max}$ of the channel 5 at the level of the cap 14 is 1300 µm and the width $L_{min}$ at the level of the bottom wall 10 is 700 µm. An angle of inclination a of approximately 26° is then obtained between the sides 11a, 11b and the cap.

These examples of narrowing of the channel 5 at the edge thereof are given by way of illustration and other arrangements (not represented) are possible. Thus, in a variant of FIG. 6, the sides can be inclined in an opposite direction, so as to form an acute angle no longer with the surface of the cap but with the surface of the bottom wall. The depth at the edge of the channel 5 is then defined by the distance along the Z-axis between the side concerned and the bottom wall. Another variant is possible, in which the sides are structured so as to each form a V. More specifically, the structured side has two mutually inclined planar portions, forming an acute angle at the intersection of a first portion with the bottom wall, and an acute angle at the intersection of the second portion with the cap. The half-angle formed at the intersection of the two portions advantageously satisfies the Concus-Finn condition.

In another variant not represented, the bottom wall 10 is not planar, but structured so as to be in the form of a "V", in transverse cross section. More specifically, the bottom wall can be formed by two portions, each of which meets the corresponding side, and in which the intersection of the two portions defines an angle less than 180°, and advantageously less than 90°.

In another variant not represented, the sides and/or the bottom wall have (has) a curved form, in transverse cross section. The sides of the curved form can be arranged to form an acute angle at the intersection with the cap which advantageously satisfies the Concus-Finn condition.

The capillary flow in the channel 5 is obtained by the fact that the wetting angle of the liquid sample on the internal surface of the channel 5, at the level of the triple line, is less than 90°. The surface of the channel 5 is then said to be hydrophilic. A wetting motive force then ensures the flow of the liquid in the channel 5. This wetting property of the internal surface of the channel 5 can be obtained or reinforced by a surface chemical treatment, notably by plasma, for example $O_2$ plasma, which makes it possible to reduce the wetting angle of the liquid in the channel 5.

The wettability, that is to say the wetting angle that the liquid forms on the surface concerned at the level of the triple line, can be identical for all the internal surface of the channel 5. However, the production of the sample-collecting device 1 in two distinct elements A, B allows a specific surface treatment of the different zones or internal surfaces of the channel 5. This surface treatment is then performed before the insertion of the male part 9 into the female part 12, and all the more easily when the channel 5 has an open transverse section over its longitudinal part. Thus, at least a portion of the surface of the bottom wall 10, at least a portion of the surface of the sides 11a, 11b of the channel 5 and/or at least a portion of the surface of the cap 14 can exhibit a different wettability from the wettability of the other surfaces of the channel 5. In other words, the surface of the cap 14, that of the sides 11a, 11b and/or that of the bottom wall 10 exhibits (exhibit), entirely or partially, a different wettability from the other internal surfaces. This localized treatment of the surface of the cap 14, of the surface of the sides 11a, 11b and/or the surface of the bottom wall 10 of the channel 5 thus makes it possible to modify the wetting angle on the treated surface and can thus modify the overall form of the liquid/gas interface particularly at the level of the triple line. This specific treatment can then have a beneficial effect in order, in particular, to avoid the formation of a gas bubble in the channel 5.

The sample-collection device 1, in particular the male part 9 and the female part 12, can be produced, for example, by a technique of molding or of injecting a plastic material such as polycarbonate, polypropylene, polyethylene, cyclo-olefine-copolymer (COC), cyclo-olefin-polymer (COP), or any other material that may be appropriate.

To guarantee an effective molding and mold-stripping of the second element B, it is advantageous to produce the female part 12 in conical form to favor its mold-stripping in a single X-axis. The second element can thus be produced in a mold with a single mold-stripping axis.

In parallel, the form of the first element A, in particular in its male part 9, must take account of these conical forms to ensure, on assembly, hermetic contact between different walls. This part can thus be produced in a mold with a single mold-stripping axis along the Z-axis.

The material forming the male 9 and female 12 parts is preferably transparent to visible and/or infrared radiation, in particular when an analysis of the liquid sample by optical means is provided.

The sample-collection device 1 can have an overall length, along the X-axis, of on the order of a few centimeters, for example two centimeters. The contact surface 2 can have a surface measuring a few square centimeters, for example 2 cm×1 cm. The collection opening can have a length of a few millimeters, for example 5 mm, over a width of 0.5 mm to 1 mm. The male part 9 can have a length and a width of a few millimeters, for example 10 mm×5 mm, for a thickness of a few hundreds of microns or even a few millimeters, for example 1 mm. The channel 5 can have a length of a few millimeters or centimeters, a width of a few hundred microns to a few millimeters, and a thickness on the order of a few tens of microns to a few millimeters. As an example, the analysis chamber can have a length, along the X-axis), of 6.5 mm, a width, along the axis Y, of 3 mm at its widest zone, and a depth, along the Z-axis, of 150 µm. These orders of magnitude are given by way of illustration only.

The sample-collection device 1 can be used to take a sample of any type of liquid, for example a biological liquid, possibly bodily liquid, such as blood, urine, or the like. The sample-collection device 1 makes it possible to take a sample of the liquid of interest to proceed with a chemical and/or biological analysis thereof.

The channel 5, in particular at the level of its analysis chamber 20, can be functionalized by a reagent intended to react with the liquid sample. The reagent can be deposited by a drying method, which leads to a surface deposition in the channel 5, or a freeze-drying method, which leads to a volume deposition.

To perform the deposition of the reagent, the latter is deposited in liquid phase in the desired zone of the channel 5, for example in the analysis chamber 20, before any introduction of the male part 9 into the female part 12. In the drying case, the evaporation of the liquid solvent can be performed at room temperature and atmospheric pressure, or even in a vacuum. In the freeze-drying case, the solvent containing the reagent is solidified and then the solvent is sublimated. The freeze-dried reagent then takes the form of a porous volume that can be dissolved in contact with the liquid sample. It is also possible to produce a biological or chemical functionalization (DNA, antibody, proteins, etc.) of the wall of the sample-collection device 1, in particular the bottom wall 10 of the channel 5, by methods of chemical coupling with covalent bonds between the species.

It will be understood that the production of the sample-collection device 1 in two elements distinct from one another makes it possible to simplify, shorten, and render more accurate the steps of deposition of the reagent in dried or freeze-dried form. In effect, the deposition of the solvent containing the reagent can be performed directly in the desired zone, without it being necessary to introduce it through the input of the channel 5 for it to then migrate to the analysis zone. It is then possible to obtain a deposition of the reagent that is particularly uniform, which is a factor of quality for the analysis of the sample performed subsequently, or else to localize the reagent at a chosen fluidic point, or else to localize several distinct reagents at distinct points of the fluidic channel 5 according to the need to produce a reaction of mixing more than one reagent. The steps of evaporation or of sublimation of the solvent are also made faster inasmuch as the evaporation or sublimation surface is increased by the fact that the transverse section of the channel 5 is open over all of a longitudinal part, and not just along the transverse part.

The sample-collection device 1 can be used as a disposable consumable thus allowing an analysis of the sample by appropriate means, possibly performed outside of an analysis laboratory.

The analysis means can be based on an analysis of the optical signal emitted by the liquid sample or modified by the latter, the walls of the male part 5 and the female part 12 allowing the transmission of the optical signal to be measured, and possibly the transmission of an excitation signal emitted by the analysis means towards the liquid sample. As an example, the analysis chamber can be subjected to an excitation light signal, in which case an optical sensor is arranged so as to detect a light signal emitted by the liquid sample in response to the absorption of the excitation signal or an optical signal modified by the transmission of the liquid sample. The wavelengths of the optical signals can be in the visible and/or in the infrared range, and the male and female parts 9, 12 are made of a material transparent to these wavelengths.

The analysis means can also be based on an electrical analysis of the liquid sample and can comprise one or more electrodes arranged in the analysis chamber of the channel 5 and linked electrically to a voltage source.

Some embodiments use thin-film deposition to form electrodes and contact tracks. This makes it possible to bring the contact to the heel of the first element A.

FIG. 7 is a front view of a sample-collecting sample-collection device 1 according to another embodiment in which the vent connecting to the open air emerges at the level of the contact surface. As shown in FIG. 7, the male part 9 is housed in the female part 12 such that the end of the peripheral wall 13 of the female part 12 abuts against the surface 24 of the heel 23 and the end transverse wall 17 of the male part 9 emerges at the level of the contact surface 2.

The channel 5 comprises a first portion that extends from the input end 4 and an analysis chamber 20 that has a width greater than that of the first portion and that is situated in the continuity of the first portion.

At the level of the second end 8 of the channel 5, a vent 21 connecting to the open air communicates with the analysis chamber 20 via a duct whose width is less than that of the analysis chamber 20 and than that of the vent 21. Because its width is different from that of the vent, this duct promotes the ability to stop liquid flow.

The vent 21 takes the form of a groove formed at the level of the top face of the male part 9. This groove extends from the duct to emerge at the level of the contact surface 2. This embodiment makes it possible to avoid having to form an emergent opening at the level of the peripheral wall 13 of the female part 12.

In an alternative embodiment, the vent takes the form of a groove formed at the level of the bottom face of the male part 9, the duct for fluidic communication with the analysis chamber extending along the thickness of the male part 9. The peripheral wall of the female part 12 comprises a part that forms a cap for closing the open transverse section of the vent.

FIG. 8 is a front view of a sample-collecting device 1 whose male part 9 is introduced into the female part 12 according to an embodiment in which an analysis chamber 20 of the channel 5, which is arranged at the level of the bottom face of the male part 9 opposite the top face, comprises an absorbent membrane 27 that is impregnable by the liquid sample.

In this example, the channel 5 comprises a first portion that extends from the input end 4, at the level of the top face of the male part 9 and an analysis chamber 20 that has a width greater than that of the first portion, that is situated in the fluidic continuity of the first portion, and that is situated at the level of the bottom face of the male part 9.

The first portion and the analysis chamber communicate via a duct that extends along the thickness of the male part 9. Preferably, the duct emerges in a central zone of the analysis chamber 20.

A vent 21 connecting the channel 5 to the open air extends between the analysis chamber 20 and, in this example, the contact surface 2. The vent 21 could also emerge at the level of a longitudinal edge of the male part 9, the peripheral wall 13 of the female part 12 then comprising a through opening situated facing the orifice of the vent 21.

The peripheral wall 13 of the female part 12 comprises a part that forms a cap closing the open transverse section of the analysis chamber so as to ensure the containment of the channel 5.

In the illustrated embodiment, the analysis chamber 20 has a form, in the X-Y plane, that is substantially circular.

However, any other form can be suitable. The analysis chamber 20 comprises a membrane 27 capable of absorbing the liquid sample by impregnation from a face of the membrane parallel to the X-Y plane at the level in which the duct of the channel 5 emerges. This results in an essentially vertical impregnation of the membrane 27 by the liquid sample. Such impregnation is faster and more uniform than a longitudinal impregnation resulting from the case in which the membrane is situated in the same plane as the first portion of the channel 5.

This membrane can consist of a stack of several porous materials. This makes it possible to ensure filtering, pumping, mixing, and/or analysis functions by migration of the biological sample by capillarity or impregnation through this membrane.

FIGS. 9a to 9d are schematic representations, in longitudinal cross section, of a part of the sample-collecting device 1 represented in FIG. 8, for different moments of the flow of the liquid sample in the channel 5.

In this example, the analysis chamber 20 is arranged at the level of a bottom face 28, opposite the top face 16 of the male part 9. The female part 12 comprises a part of its peripheral wall that forms a second cap 30. The second cap 30, at the level of its internal face, closes the transverse section of the analysis chamber 20.

Figure 9A:
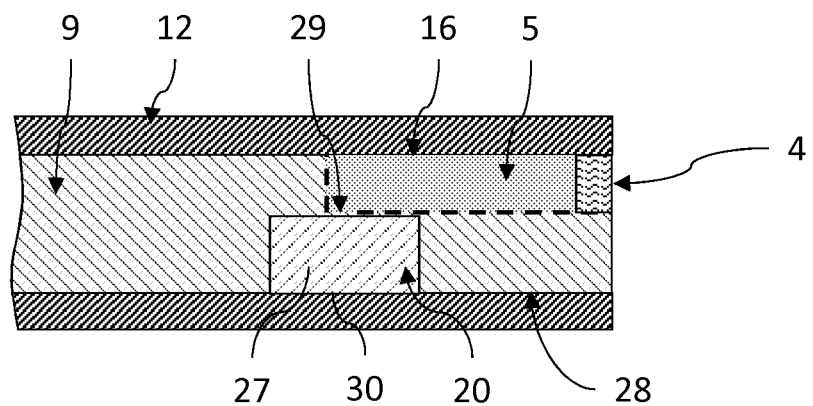
FIGS. 9a to 9d are schematic representations, in longitudinal cross section, of a part of the sample-collecting device represented in FIG. 8, for different moments of the flow of the liquid sample in the channel.
Figure 9B:
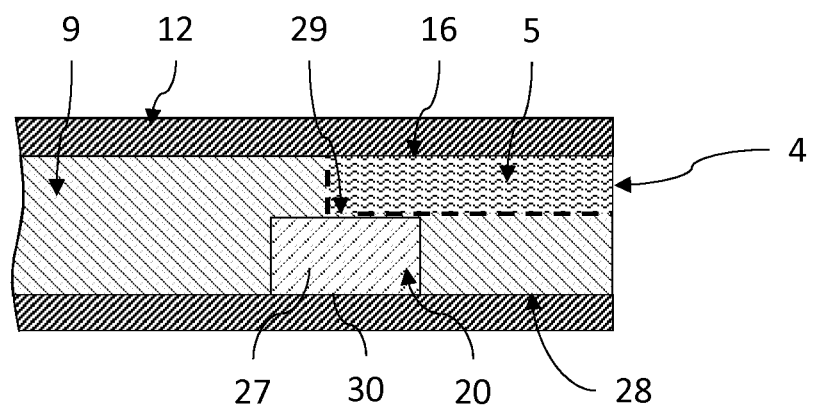
Figure 9C:
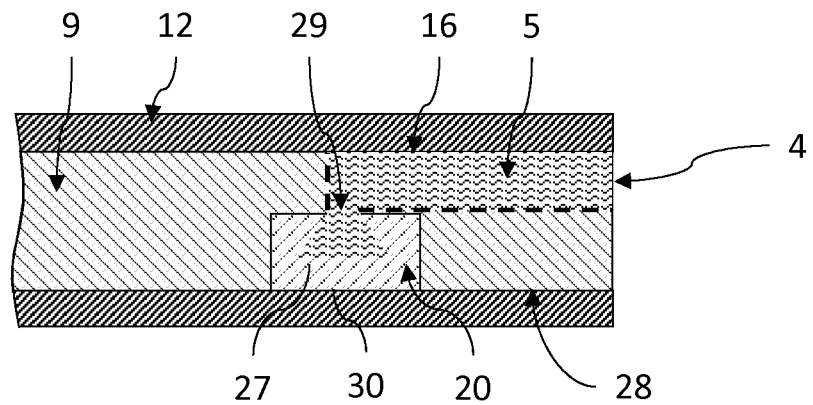
Figure 9D:
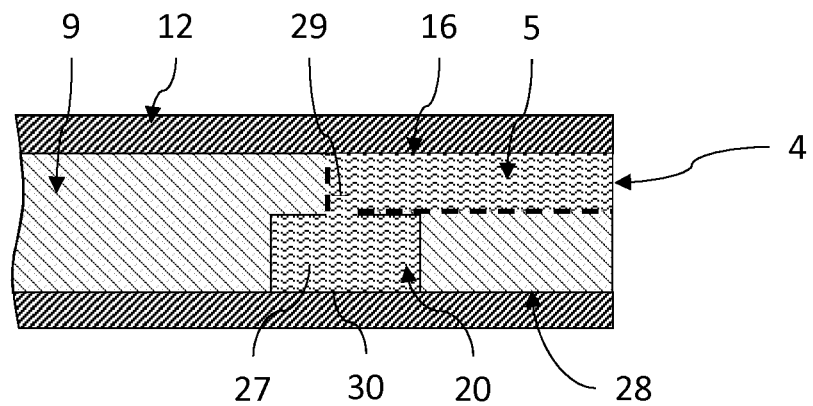

The liquid sample is introduced into the first portion of the channel 5 represented here by dotted lines from the input end 4 (FIG. 9a) and flows to the duct 29 for fluidic communication with the analysis chamber (FIG. 9b). For clarity, the duct 29 is represented by a break in the dotted line illustrating the bottom wall although it is formed by a portion of channel 5 extending along the thickness of the channel 5, along the Z-axis of the reference frame represented in FIG. 8. The liquid sample flows through the duct 29 to the analysis chamber 20 and comes into contact with the central part of the membrane 27, which provokes the impregnation thereof by the liquid sample (FIG. 9c). The impregnation is done in the thickness of the membrane 27 and continues to the circular edge of the membrane 27. When the impregnation of the membrane is finished (FIG. 9d), an analysis of the liquid sample can then be performed, for example by optical means capable of detecting a change of color of the membrane or of the bottom face of the membrane.

The method for producing a sample-collecting device 1 according to one of the embodiments that have just been described comprises the steps of: producing a first element A, that comprises a male part 9, the latter comprising at least one channel 5 with open transverse section, extending longitudinally between a first input end 4 and a second end 8, the channel 5 being formed by a channel-bottom longitudinal wall 10 bordered by two lateral walls 11a, 11b forming the sides of the channel 5; producing a second element B, distinct from the first element A, comprising a female part 12, the latter comprising a peripheral wall 13 that transversely delimits a cavity intended to house the male part 9, a part 14 of the peripheral wall 13 forming, when the female part 12 houses the male part 9, a cap closing the transverse section of the channel 5, functionalizing a zone of the channel 5 forming an analysis chamber 20; and introducing the male part 9 into the female part 12.

The functionalization of a surface should be understood here to mean the deposition, on the surface, of at least one element intended to interact with the liquid sample, for example at least one dried or freeze-dried reagent, or the immobilization by covalent chemical bond of biological or chemical species, at least one electrode, at least one absorbent membrane.

The method for analyzing a liquid sample is performed using a sample-collecting device 1 according to one of the embodiments that have just been described. Analysis comprises the steps of introducing the male part 9 into the female part 12 such that the cap 14 of the female part 12 closes the transverse section of the channel 5; depositing a liquid sample at the level of the first input end 4 of the channel 5, such that the liquid sample flows by capillarity to an analysis chamber 20 of the channel 5; and analyzing the liquid sample situated in the analysis chamber 20.

Prior to the step of introduction of the male part 9 into the female part 12, at least a part of the internal surface of the channel 5 is advantageously functionalized by depositing a reagent intended to react with the liquid sample, an absorbent membrane, even electrodes.

The invention is not limited to the exemplary embodiments that have just been described. Various modifications can be made thereto by a person skilled in the art.

As an example, the channel 5 can comprise a portion extending longitudinally in serpentine form or a portion having a succession of direction-changing bends.

The channel 5 can comprise, communicating with a first portion which extends from the input end 4, a plurality of portions all linked to the first portion and each extending to its own analysis chamber.

The male part 9 can comprise several channels, each extending from its own input end 4, possibly intended to emerge at the level of the same collection opening of the contact surface, or at the level of mutually distinct collection openings. Thus, at least one second channel, with open transverse section, is arranged at the level of a bottom face of the plate opposite the top face, possibly communicating with the channel situated at the level of the top face, and in which a part of the peripheral wall of the female part 12 is intended, when the female part 12 houses the male part 9, to form a second cap closing the transverse section of the second channel.

Figure 10A:
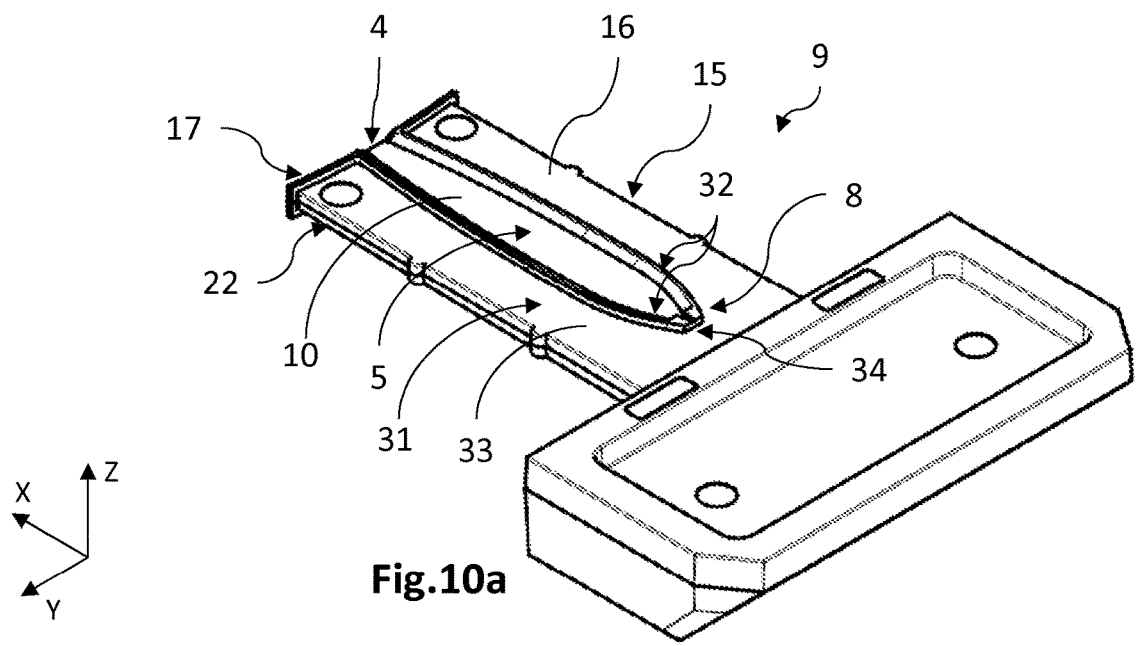
FIGS. 10a, 10b and 10c are views, respectively in perspective, from above and from below, of a male part according to another embodiment in which the channel is surrounded at least partly by a peripheral zone of greater depth.
Figure 10B:
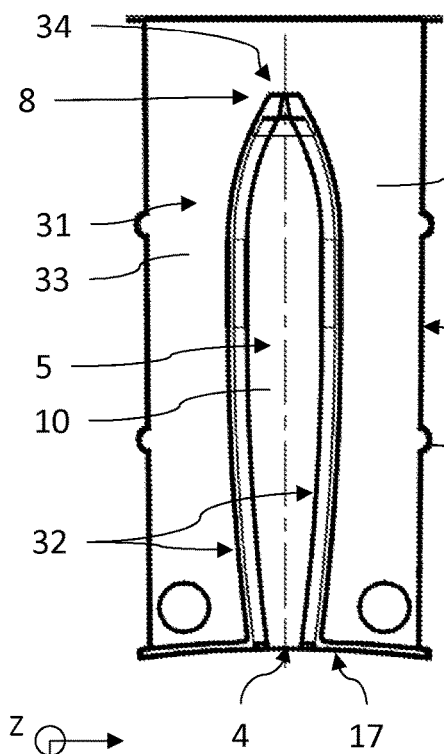
Figure 10C:
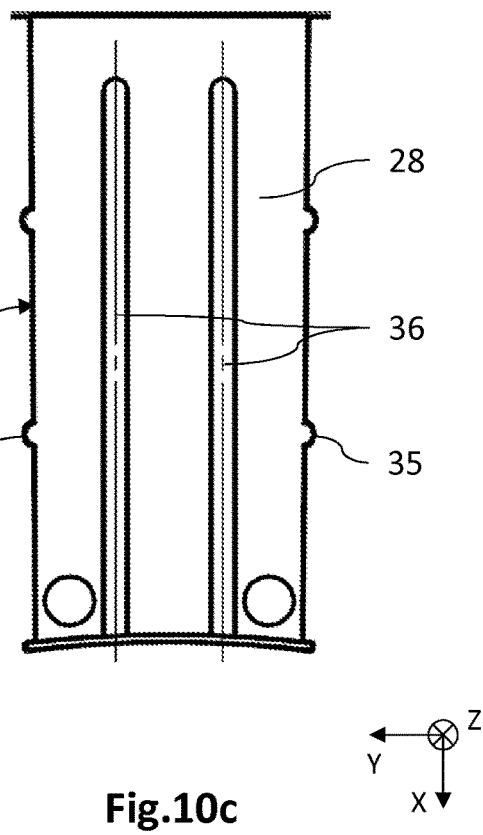

There now follows a description, referring to FIGS. 10a-10c, 11a-11c, 12a-12b, and 13a-13b, of a male part 9 according to another embodiment and adapted to cooperate with the female part 12 as described previously. FIG. 10a is a perspective view of the male part 9 and FIGS. 10b and 10c are respectively partial views from above and from below of the male part 9 illustrated in FIG. 10a.

The male part 9 is distinguished from the examples described previously mainly in that the channel 5 is bordered by a peripheral zone 31, or peripheral void, whose depth is greater than the central depth $P_c$ of the channel 5.

More specifically, the plate 15 of the male part 9 comprises, at the level of its top face 16, delimiting lateral-walls 32 that extend from the end transverse wall 17 of the plate 15 along the longitudinal X-axis of the channel 5. These delimiting lateral-walls 32 are portions protruding with respect to the top face 16 of the plate 15. They thus segregate two zones of the top face 16 of the plate 15 into a first zone and a second zone. The first zone forms the channel 5, delimited by the bottom surface 10 and the internal faces 32a (corresponding to the sides 11a, 11b) of the delimiting lateral-walls 32, of central depth $P_c$ defined as the distance between the bottom surface 10 and a plane passing through the top faces 32b of the delimiting lateral-walls 32, along the Z-axis substantially orthogonal to the bottom surface 10. The second zone is a peripheral zone 31 that extends at least partly around the channel 5, delimited by the top face 16 of the plate 15 outside of the bottom surface 10, and by the external faces 32c (opposite the internal faces 32a) of the delimiting lateral-walls 32. This peripheral zone forms a peripheral void of a depth $P_p$ that is greater than the central depth $P_c$ of the channel 5.

Thus, the top face 16 of the plate 15 comprises a bottom surface 10 of the channel 5 and a peripheral surface 33 of the peripheral zone 31 segregated from one another by the delimiting lateral-walls 32 protruding with respect to the top face 16. The peripheral surface 33 forms a recess with respect to the bottom surface 10 so that the peripheral zone 31 forms a void of a depth greater than the central depth $P_c$ of the channel 5.

Figure 11A:
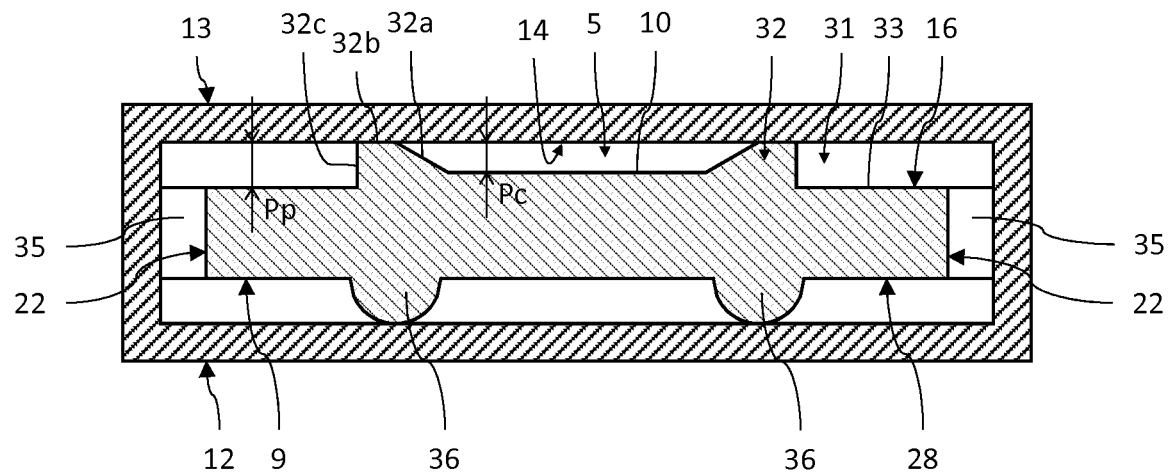
FIGS. 11a to 11c are schematic views in transverse cross section of the collection device when the female part houses the male part according to this other embodiment.

As FIG. 11a shows, each delimiting lateral wall 32 comprises a top face 32b, intended to be in contact with the cap 14 when the female part 12 houses the male part 9, the top face 32b linking the internal face 32a and the external face 32b. The internal face 32a of each delimiting lateral wall 32 is preferably inclined with respect to the bottom surface 10 so as to form an acute angle with the cap 14. This angle is less than 45°, and in some cases is, for example 30°. The external face 32c has an orientation with respect to the cap 14 so as to form an angle greater than the acute angle of the internal face 32a, preferably greater than or equal to 60°, and preferably of the order of 90°, so as to form an abrupt variation of the depth at the level of the peripheral zone.

As FIG. 10b shows, the delimiting lateral-walls 32 are distant from one another at the level of the end face 17 of the plate 15 to form together the input 4 of the channel 5, then extend along the longitudinal X-axis of the channel 5, then converge towards one another at the level of the second end 8 of the channel 5 to form a duct 34 for discharging gas possibly contained initially in the channel 5 (described in detail later, with reference to FIGS. 13a and 13b) that allows the fluidic communication between the channel 5 and the peripheral zone 31.

In a purely illustrative manner, the central depth $P_c$ of the channel 5 can be approximately 150 μm while the depth $P_p$ of the peripheral zone 31 is approximately 180 μm. The internal faces 32a can be inclined by approximately 30° with respect to the cap. They can be spaced apart by approximately 0.70 mm at the level of the input 4 of the channel 5, by approximately 1.5 mm in the middle of the channel, and approximately 0.25 mm at the level of the second end 8 of the channel 5.

In this example, the peripheral zone 31 extends at the level of the top face 16 of the plate 15, but also at the level of the bottom face 28 and of the longitudinal edges 22. To keep a substantially constant depth of the peripheral zone, spacers are arranged at the level of the bottom face 28 and of the longitudinal edges 22.

Thus, spacers 35 are arranged at the level of the longitudinal edges 22, in the form of spacing blocks protruding with respect to each of these edges 22. They maintain a substantially constant spacing between the facing face of the peripheral wall 13 of the female part 12 and each of the longitudinal edges 22, this spacing having a value greater than the central depth of the channel 5, for example a value substantially equal to the depth $P_p$.

As FIG. 10c shows, spacers 36 are also arranged at the level of the bottom face 28 of the plate 15, in the form of spacing rails or walls protruding with respect to this bottom face 28. They also maintain a substantially constant spacing between the facing face of the peripheral wall 13 of the female part 12 and the bottom face 28, this spacing having a value greater than the central depth of the channel 5, for example a value substantially equal to the depth $P_p$.

Figure 11B:
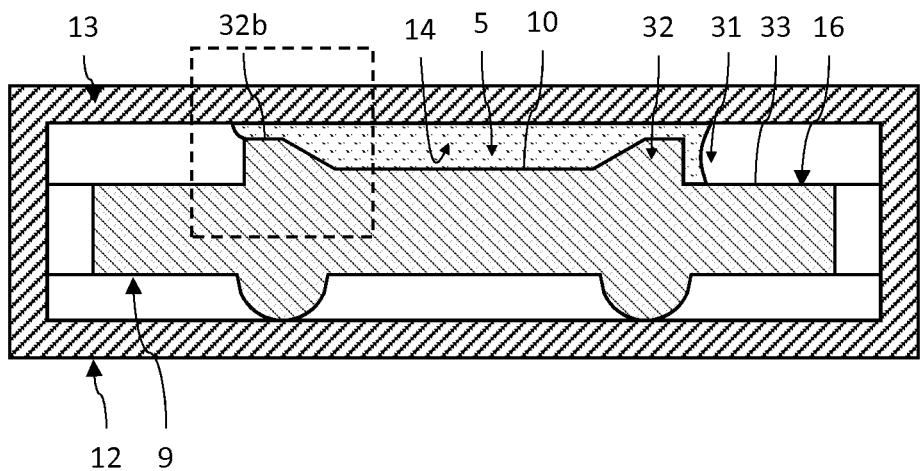

FIGS. 11a and 11b are schematic views in transverse cross section of a part of the collection device 1 when the female part 12 houses the male part 9, at the level of the channel 5, when the delimiting walls 32 are in contact with the cap 14 (FIG. 11a) and when a local loss of contact occurs between the delimiting walls 32 of the channel 5 and the cap 14 (FIG. 11b).

In FIG. 11a, the male part 9 is surrounded by the peripheral wall 13 of the female part 12. The top face 16 is structured so as to comprise the bottom surface 10 of the channel 5 and a peripheral surface 33 of the peripheral zone 31, these surfaces 10, 33 being segregated from one another by the delimiting lateral-walls 32. The peripheral surface 33 forms a recess with respect to the bottom surface 10 of the channel 5 so as to form a peripheral void 31 of a depth $P_p$ greater than the central depth $P_c$ of the channel 5.

A configuration in which the channel 5 is surrounded at least partly by a peripheral zone 31 of greater depth makes it possible to limit the leaks of liquid out of the channel 5.

In effect, as FIG. 11b shows, when a local loss of contact occurs between the cap 14 and a delimiting wall 32 of the channel 5, a liquid is likely to leak. However, when the liquid flows by capillarity out of the channel 5 and joins the peripheral zone 31, because of the depth $P_p$ being greater than the central depth $P_c$ of the channel 5, the motive forces of capillarity exhibit an intensity lower than that of the forces of capillarity in the channel 5. Thus, the liquid flows predominantly along the channel 5 and not out of the channel in the peripheral zone 31. A predominant filling of the channel 5 is thus assured while limiting the leaks out of the channel 5.

Figure 11C:
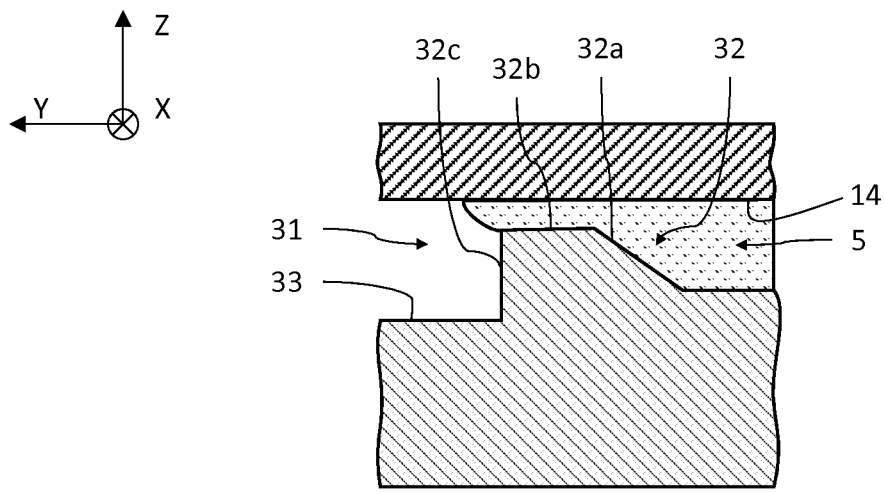

FIG. 11c is a detailed view of the dotted line part of FIG. 11b. As FIG. 11c shows, the delimiting wall 32 is structured at the level of its external face 32c to have, on the one hand, a sharp edge at the intersection between its top face 32b and its external face 32c, and, on the other hand, an abrupt increase in the local depth. A sharp edge is a line of intersection between two planes where an angle can be defined. The abrupt increase can be obtained by an inclination of the external face 32c with respect to the cap 14 to form an angle greater than the angle of inclination of the internal face 32a with respect to the cap. This configuration avoids having liquid flow out of the channel 5 into the peripheral zone 31 from a local loss of mechanical contact between the cap 14 and the top face 32b.

In this example, the internal face 32a forms an angle of 30° with the cap 14 whereas the external face 32c forms an angle of approximately 90°. Because of this structure, the triple line of the liquid in contact with the delimiting wall 32 is blocked at the level of the sharp edge, all the more so as the capillary motive forces exhibit locally, at the level of the peripheral void 31, an intensity greatly reduced because of the abrupt increase in the local depth. Thus, the liquid is trapped at the level of the local space between the delimiting wall 32 and the cap 14 and does not flow out of the channel 5.

Figure 12A:
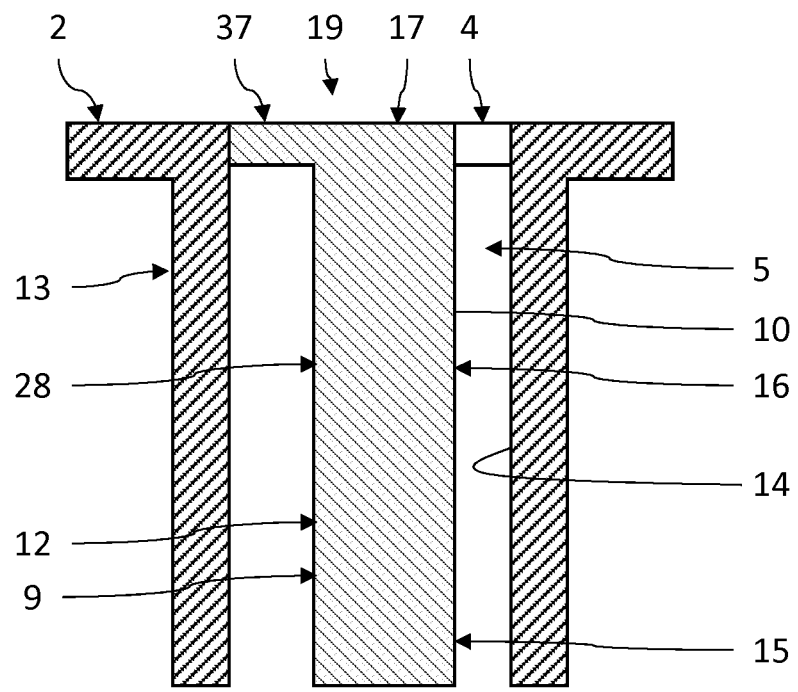
FIGS. 12a and 12b are schematic views in longitudinal cross section of the collection device at the level of the input of the channel.
Figure 12B:
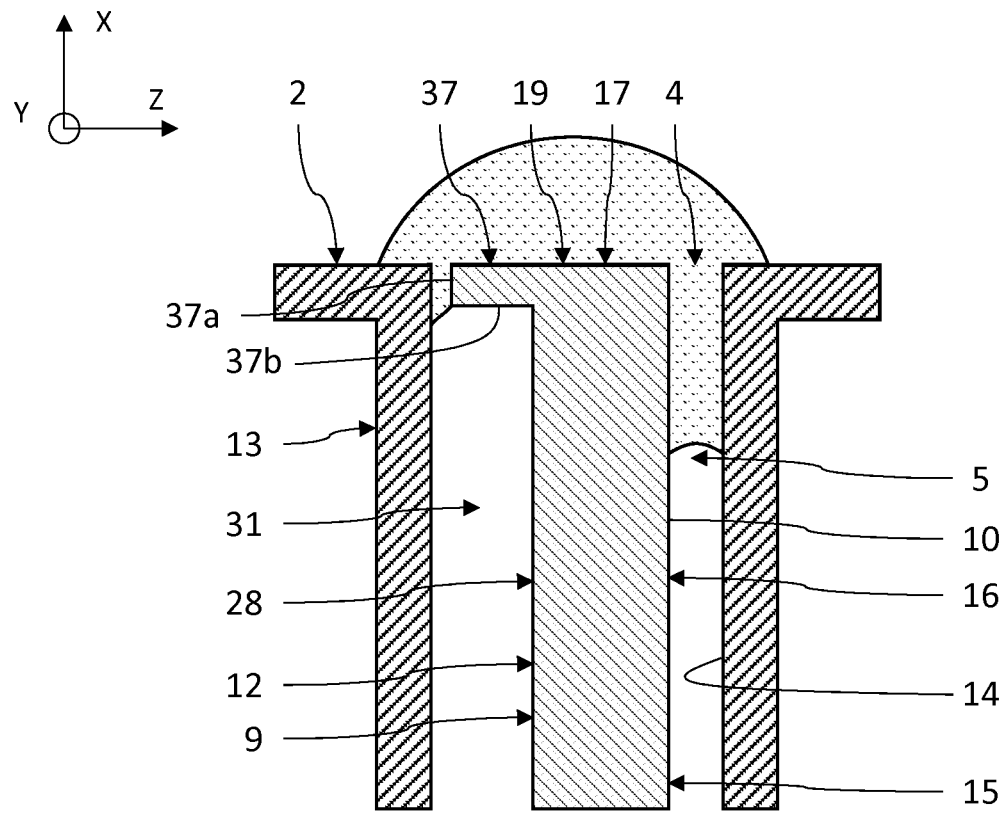

FIGS. 12a and 12b are schematic views in longitudinal cross section of a part of the collection device 1 when the female part 12 houses the male part 9, at the level of the input 4 of the channel 5 and of the contact surface 2, which in this case is a collection cup, when a sealing transverse wall 37 is in contact with the peripheral wall 13 (FIG. 12a) and when a local loss of contact occurs between the sealing transverse wall 37 and the peripheral wall 13 (FIG. 12b).

As shown in FIG. 12a, in conjunction with FIGS. 10a to 10c, the plate 15 can also comprise a sealing transverse wall 37 situated at the level of the input-end face 17. The sealing transverse wall 37 extends circumferentially at the edge of the plate 15 and protrudes with respect to the top 16 and bottom 28 faces and the lateral edges 22 apart from the input 4 of the channel 5. It is intended to come into contact with the peripheral wall 13 and be flush with the collection surface of the contact cup when the female part 12 houses the male part 9. The sealing wall 37 has a dimension such that it comes into contact with the circumferential edge of the collection opening 19, apart from at the level of the input 4 of the channel 5. Thus, when a liquid sample is deposited on the contact surface 2, which in this case is a contact cup or collection cup, it is introduced into the channel 5 through the input 4 situated at the level of the collection opening 19.

As FIG. 12b shows, if a local loss of mechanical contact occurs between the sealing transverse wall 37 and the peripheral wall 13, liquid is likely to be introduced into the peripheral zone 31. However, the capillary motive forces exhibit a greater intensity at the level of the channel 5 than at the level of the peripheral zone 31, which is reflected by a predominant capillary flow of the liquid in the channel 5 compared to the peripheral zone 31.

Furthermore, so as to avoid having liquid flow into the peripheral zone 31 from a local loss of mechanical contact between the peripheral wall 13 and the sealing transverse wall 37, the latter is structured at the level of its internal face 37a (oriented towards the peripheral zone 31) to have, on the one hand, a sharp edge at the intersection between its top face 37b and its internal face 37a, and, on the other hand, an abrupt increase in the local depth. The abrupt increase can be obtained by an orientation of the internal face 37a with respect to the peripheral wall 13 so as to form an angle greater than 45°, preferably greater than 60°, and preferably close to or equal to 90° as illustrated in FIG. 12b. Because of this structuring, the triple line of the liquid in contact with the sealing wall 37 is once again blocked at the level of the sharp edge, all the more so as the capillary motive forces exhibit locally, at the level of the peripheral zone 31, an intensity that is greatly reduced because of the abrupt increase in the local depth. Thus, the liquid is trapped at the level of the local space between the sealing wall 37 and the peripheral wall 13 and does not flow into the peripheral zone 31.

Figure 13A:
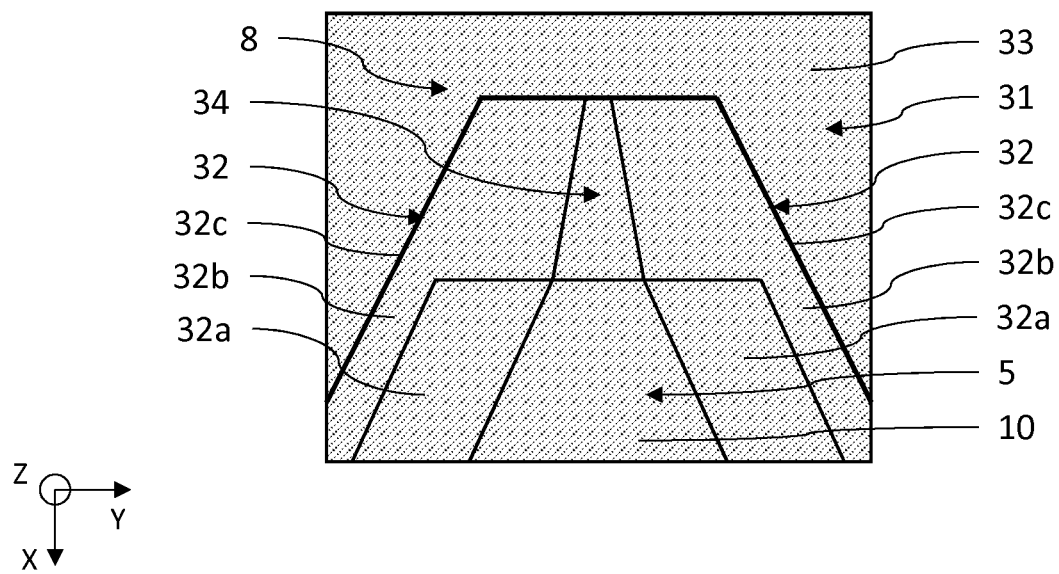
FIGS. 13a and 13b are schematic views of the vent of the channel, seen from above (FIG. 13a) and in longitudinal cross section (FIG. 13b).
Figure 13B:
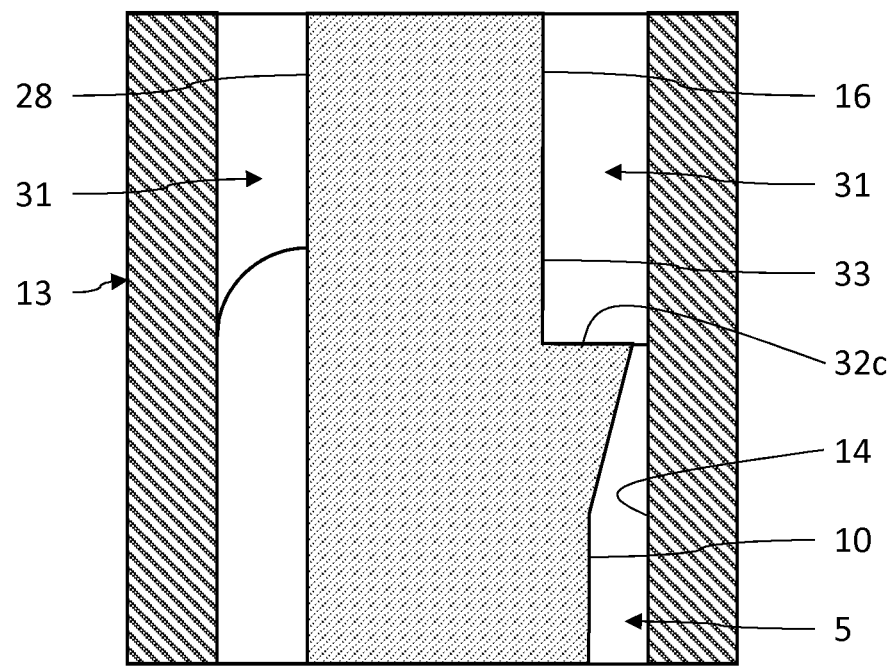

FIGS. 13a and 13b are schematic views of the end of the channel at the level of the terminal end of the channel 5, seen from above (FIG. 13a) and in longitudinal cross section (FIG. 13b).

As FIG. 13a shows, the delimiting lateral-walls 32 converge towards one another and meet at the level of the second end 8 of the channel 5. They do however comprise a local structuring in the form of a duct 34 ensuring a fluidic communication between the channel 5 and the peripheral zone 31 situated downstream of the channel 5. This duct has a vent function and makes it possible to discharge gas possibly present initially in the channel 5, thus limiting the risks of bubble-formation in the channel 5 upon the capillary introduction of the liquid sample.

In this example, the duct 34 narrows its width and reduces its depth with increased distance away from the channel 5. Thus, at the level of its end opposite the channel 5, and in a purely illustrative manner, the duct can have a minimum width of approximately 70 μm and a minimum depth of approximately 30 μm.

As FIG. 13b shows, a recess between the bottom surface 10 and the peripheral surface 33 forms a sharp edge and an abrupt increase in the local depth. The abrupt increase in the local depth can be obtained by orienting the external face 32c of the delimiting walls 32 at the level of the duct 34 with respect to the cap 14 at an angle greater than 45°, preferably greater than 60°, and preferably close to or equal to 90° as illustrated in FIG. 13b. Because of this structure, the triple line of the liquid in contact with the bottom surface of the duct is once again blocked at the level of the sharp edge, all the more so as the capillary motive forces exhibit locally, at the level of the peripheral zone 31, an intensity that is greatly reduced because of the abrupt increase in the local depth. Thus, the liquid is trapped at the level of the end of the duct 34 and does not flow into the peripheral zone 31.

Generally, the sample-collection device 1 for collecting a liquid sample by capillarity can comprise: a channel 5 that extends longitudinally between a first input end 4 and a second end 8, the channel 5 being bordered laterally by two delimiting lateral-walls 32, and, along a depth axis of the channel, by a bottom longitudinal surface 10 and a surface forming a cap 14 intended to be in contact with the delimiting lateral-walls 32, the channel 5 being surrounded transversely by a peripheral zone 31 delimited by the delimiting lateral-walls 32, and along the depth axis by the surface forming the cap 14 and a peripheral opposite surface 33, and the peripheral zone 31 having a depth, between the cap 14 and the peripheral surface 33, greater than a depth of the channel 5.

Depth should be understood to mean the dimension between the surface forming the cap 14 and the opposite surface along an axis substantially orthogonal to the surfaces. The opposite surface is the bottom surface 10 in the case of the channel 5 or the peripheral surface 33 in the case of the peripheral zone 31.

Each delimiting lateral wall 32 can comprise an internal face 32a oriented towards the channel 5, an opposed external face 32c oriented towards the peripheral zone 31, and a top face 32b linking the internal 32a and external 32c faces and intended to be in contact with the cap 14. The external face 32c can have a sharp edge with respect to the top face 32b. A sharp edge should be understood to be a line of intersection between the planes passing through the external and top faces, at the level of which an angle can be defined.

The external face 32c of each delimiting lateral wall 32 can have an angle of inclination with respect to the cap 14 greater than or equal to 45°, preferably greater than or equal to 60°, and preferably substantially equal to 90°.

The channel 5 can be situated on a top face 16 of a plate 15, the peripheral zone 31, forming a peripheral void, extending on the top face 16 at least partly around the channel 5. The peripheral surface 33 is thus set back with respect to the bottom surface 10. The peripheral zone 31 can also extend at the level of a bottom face 28 opposite the top face 16 of the plate 15, and/or also extend at the level of longitudinal edges 22 of the plate 15 linking the top face 16 and the bottom face 28.

At least one spacer 36 can be provided on the top face 28 for coming into contact with the peripheral wall 13. At least one spacer 35 can be provided at the level of each longitudinal edge 22 to be in contact with the peripheral wall 13. Thus, when the peripheral wall 13 is in contact with one of the spacers 35, 36, the peripheral zone 31 locally exhibits a depth $P_p$ greater than a central depth $P_c$ of the channel.

The plate 15 can comprise an end transverse face 17 at the level of which an input 4 of the channel 5 is situated, the input 4 being situated at the level of a collection opening 19 of the peripheral wall 13. The plate 15 can comprise a sealing transverse wall 37 that extends partly circumferentially at the edge of the end transverse face 17, apart from on a part of the top face 16 so as to form the input 4 of the channel 5. The sealing transverse wall 37 can have a dimension, along an axis at right angles to a top 16 or bottom 28 face of the plate 15, greater than a central depth of the channel 5.

The channel 5 can comprise, at the level of its second end 8, a duct 34 for fluidic communication between the channel 5 and the peripheral zone 31. The duct 34 can exhibit a reduction of its depth and/or of its width. The delimiting lateral-walls 32 can meet at the level of the second end 8 and have a structuring forming the duct 34. The bottom surface 10 at the level of the duct 34 can form a sharp edge with an external face 32c of the delimiting walls 32. The external face 32c locally links the peripheral surface 33 to the bottom surface 10 at the level of the duct 34. It can have an angle with respect to the cap 14 that is greater than or equal to 45°, preferably greater than or equal to 60° and preferably of the order of 90°.

Having described the invention and a preferred embodiment thereof, what is claimed as new and secured by Letters Patent is:

1. An apparatus comprising a device for collecting a liquid sample by capillarity, said device comprising a first element and a second element, wherein said first element comprises a male part, wherein said second element, which is distinct from said first element, comprises a female part, wherein said male part comprises a channel having an transverse section, wherein said channel extends along a longitudinal axis between a first end and a second end, wherein said first end is an input end, wherein said channel is formed by a channel-bottom longitudinal wall bordered by two lateral walls that form sides of the channel, wherein said female part comprises a peripheral wall, wherein said peripheral wall transversely delimits a cavity to house said male part, wherein a part of said peripheral wall forms a first cap to close said transverse section when said female part houses said male part, said device further comprising a plate having a rectangular transverse section and a top longitudinal face, wherein said plate forms said male part, wherein said channel is disposed at a level of said top longitudinal face.

2. The apparatus of claim 1, wherein at least one of said sides is arranged such that, when said female part houses said male part, a distance between two walls of said channel decreases towards a transverse edge of said channel, wherein said distance is measured in a plane transverse to said longitudinal axis.

3. The apparatus of claim 1, wherein said channel comprises an analysis chamber disposed at the level of said top longitudinal face.

4. The apparatus of claim 1, wherein said plate comprises a bottom longitudinal face opposite said top longitudinal face, wherein said channel comprises an analysis chamber disposed at the level of said bottom longitudinal face.

5. The apparatus of claim 1, wherein said channel comprises an analysis chamber having an open transverse section, wherein said plate comprises a bottom longitudinal face opposite said top longitudinal face, wherein said analysis chamber is disposed at said bottom longitudinal face, wherein said analysis chamber communicates with a portion of said channel that is level with said top longitudinal face, wherein a part of said peripheral wall forms a second cap that closes said transverse section when said female part houses said male part.

6. The apparatus of claim 5, further comprising a duct that emerges level with a central zone of said analysis chamber, wherein said analysis chamber is in communication with a portion of said channel that is level with said top longitudinal face via said duct.

7. The apparatus of claim 1, wherein dimensions of said male part and dimensions of said female part delimiting said cavity are chosen such that, when said female part houses said male part, said first cap bears on said top longitudinal face so as to ensure a hermetic seal of said transverse section.

8. The apparatus of claim 1, wherein said plate has a bottom longitudinal face opposite said top longitudinal face, wherein dimensions of said male part and dimensions of said female part delimiting said cavity are chosen such that, when said female part houses said male part, said first cap bears on said top longitudinal face and on said bottom longitudinal face so as to ensure a hermetic seal of said transverse section.

9. The apparatus of claim 1, wherein said first cap has a surface at least a portion of which has a wettability that differs from that of other surfaces of said channel.

10. The apparatus of claim 1, wherein said channel-bottom longitudinal wall has a surface at least a portion of which has a wettability that differs from that of other surfaces of said channel.

11. The apparatus of claim 1, wherein at least one of said two lateral walls that form sides of said channel has a surface at least a portion of which has a wettability that differs from that of other surfaces of said channel.

12. The apparatus of claim 1, wherein said second element comprises a contact surface, wherein said cavity comprises a collection opening, wherein said male part comprises an end transverse wall level with said first end of said channel, wherein said contact surface receives said liquid sample, wherein said contact surface is assembled with said female part such that said collection opening emerges at a level of said contact surface, wherein, when said female part houses said male part, said end transverse wall and said contact surface are flush with each other.

13. The apparatus of claim 1, further comprising a vent to the environment of said device, wherein said second end communicates with said vent.

14. The apparatus of claim 1, wherein said first element comprises a gripping heel on which the male part is assembled.

15. An apparatus comprising a device for collecting a liquid sample by capillarity, said device comprising a first element and a second element, wherein said first element comprises a male part, wherein said second element, which is distinct from said first element, comprises a female part, wherein said male part comprises a channel having an transverse section, wherein said channel extends along a longitudinal axis between a first end and a second end, wherein said first end is an input end, wherein said channel is formed by a channel-bottom longitudinal wall bordered by two lateral walls that form sides of the channel, wherein said female part comprises a peripheral wall, wherein said peripheral wall transversely delimits a cavity to house said male part, wherein a part of said peripheral wall forms a first cap to close said transverse section when said female part houses said male part, said device further comprising a plate that extends in a plane of said male part, wherein said plate forms a gripping heel on which said male part is assembled, wherein said plate comprises a protruding portion that faces a plate of said heel.

16. The apparatus of claim 1, wherein said channel comprises an analysis chamber that comprises at least one of a dried reagent and a freeze-dried reagent.

17. The apparatus of claim 1, wherein said channel comprises an analysis chamber that comprises an electrode.

18. The apparatus of claim 1, wherein said channel comprises an analysis chamber that comprises an absorbent membrane.

19. The apparatus of claim 1, further comprising delimiting lateral walls and a peripheral zone comprising a peripheral surface that faces said peripheral wall, wherein said peripheral zone at least partly surrounds said channel, wherein said delimiting lateral walls transversely delimit said channel and contact said first cap, wherein said delimiting lateral walls segregate said channel from said peripheral zone, wherein said channel-bottom longitudinal wall faces said first cap, wherein a distance between said peripheral surface and said peripheral wall along an axis orthogonal to said channel-bottom longitudinal wall is greater than a distance between said channel-bottom longitudinal wall and said first cap.

20. A method comprising producing a liquid sample using a sample-collecting device that comprises a first element and a second element, wherein said first element comprises a male part, wherein said second element, which is distinct from said first element, comprises a female part, wherein said male part comprises a channel having an transverse section, wherein said channel extends longitudinally between a first end and a second end, wherein said first end is an input end, wherein said channel is formed by a channel-bottom longitudinal wall bordered by two lateral walls that form sides of the channel, wherein said female part comprises a peripheral wall, wherein said peripheral wall transversely delimits a cavity to house said male part, wherein a part of said peripheral wall forms a cap to close said transverse section when said female part houses said male part, wherein said sample-collecting device further comprises a plate having a rectangular transverse section and a top longitudinal face, wherein said plate forms said male part, wherein said channel is disposed at a level of said top longitudinal face, said method comprising forming an analysis chamber and introducing said male part into said female part, wherein forming an analysis chamber comprises functionalizing a zone of said channel.

\* \* \* \* \*